US00PP21473P2

(12) United States Plant Patent
Farrow

(10) Patent No.: US PP21,473 P2
(45) Date of Patent: Nov. 16, 2010

(54) ***SPIRAEA* PLANT NAMED 'CONALEX'**

(50) Latin Name: *Spiraea japonical*
Varietal Denomination: Conalex

(75) Inventor: Michael W. Farrow, Earleville, MD (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/588,529

(22) Filed: Oct. 19, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
(74) *Attorney, Agent, or Firm*—Buchanan Ingersoll & Rooney PC

(57) ABSTRACT

A new variety of *Spiraea japonica* is provided which displays a distinctive ornamental appearance. Attractive light-green foliage is formed that commonly includes the substantial presence of bright yellow coloration unlike the 'Lemondrop' variety (U.S. Plant Pat. No. 15,016). The bright yellow coloration is particularly pronounced when the plant is grown in full sun. Also, unlike the 'Lemondrop' variety, the foliage well resists burning when grown in full sun. A dwarf mounding growth habit is displayed. Attractive medium-pink blossoms are formed on a substantially continuous basis that commonly extends from May to October. Good winter hardiness is exhibited. The plant propagates well through the rooting of cuttings.

1 Drawing Sheet

Botanical/commercial classification: *Spiraea japonica*/ Japanese *Spiraea*.

Varietal denomination: cv. Conalex.

SUMMARY OF THE INVENTION

The new *Spiraea japonica* plant of the present invention was discovered during 2007 at Earleville, Md., U.S.A., while growing in a plant nursery tended by man among plants of the 'Lemondrop' variety (U.S. Plant Pat. No. 15,016). Such plant is assumed to be a chance seedling of the 'Lemondrop' variety; however, the exact parentage of the new plant is unknown. The new plant has been carefully preserved and studied in view of its distinctive combination of characteristics. Had the new plant of the present invention not been discovered and preserved, it would have been lost to mankind.

It was found that the new *Spiraea japonica* plant of the present invention displays the following combination of characteristics:

(a) exhibits a dwarf mounding growth habit,
(b) on a substantially continuous basis forms attractive medium-pink blossoms,
(c) forms attractive light-green foliage that commonly includes substantial bright yellow coloration unlike the 'Lemondrop' variety (U.S. Plant Pat. No. 15,016), and well resists burning when present in full sun, and
(d) displays good winter hardiness.

The substantial development of bright yellow foliage coloration is particularly pronounced when the plant is grown in full sun.

The new variety well meets the needs of the horticultural industry and is particularly well suited for use as a border planting, foundation planting, or mass planting. It also can be grown to advantage in rock gardens.

Good winter hardiness has been displayed when plants were grown during the winter in containers at West Grove, Pa., U.S.A., and in the ground at Earleville, Md., U.S.A.

Plants of the new variety can be readily distinguished from those of the 'Lemondrop' variety (U.S. Plant Pat. No. 15,016). More specifically, the new variety displays a slightly larger dwarf stature, displays medium-pink blossoms unlike the mauve-pink blossoms of the 'Lemondrop' variety, and displays foliage with more yellow coloration that does not burn in full sun. The 'Lemondrop' variety lacks the substantial presence of the bright yellow foliage coloration of the new variety and forms foliage that tends to burn under full sun growing conditions.

Additionally, the new variety of the present invention can be readily distinguished from the 'Little Princess' variety (non-patented in the United States) and the 'Yan' variety (non-patented in the United States). The 'Little Princess' variety displays a larger growth habit and forms green foliage that lacks the yellow coloration of the new variety. The 'Yan' variety displays a taller and less wide growth habit than the new variety, forms darker colored flowers, and displays foliage coloration that generally lacks the brightness of the new variety.

The rooting of cuttings has been used to asexually propagate the new variety at Earleville, Md., U.S.A., and at West Grove, Pa., U.S.A. It has been found that the characteristics of the new variety are stable and are reliably transmitted from one generation to another. Accordingly, the new variety can be asexually reproduced in a true-to-type manner.

The new variety has been named 'Conalex'.

BRIEF DESCRIPTION OF THE PHOTOGRAPH

The accompanying photograph, taken during May 2009, shows a typical specimen of a plant of the new variety in color as nearly true as it is reasonably possible to make the same in a color illustration of this nature. The plant had been propagated by the rooting of a cutting, was approximately two years of age, and was being grown outdoors in a container at West Grove, Pa., U.S.A.

DETAILED DESCRIPTION

The following is a detailed description of the new variety while observing plants of approximately two years of age during September while being grown outdoors on their own roots in three-gallon containers at West Grove, Pa., U.S.A. The chart used in the identification of color is The R.H.S. Colour Chart of The Royal Horticultural Society, London, England. Common color terms are to be accorded their customary dictionary significance.

Botanical classification: *Spiraea japonica*, cv. Conalex.

*Parent.*—Likely parent *Spiraea japonica,* cv. Lemondrop.

Plant:

*Type.*—Perennial shrub, groundcover.

*Growth habit.*—Dwarf mounding.

*Height.*—Approximately 13 to 15 cm. This can be compared to a height of approximately 20 cm for the 'Yan' variety.

*Width.*—Approximately 40 cm. This can be compared to width of approximately 30 cm for the 'Yan' variety.

*Stems.*—Length: Approximately 10 cm on average. Diameter: Near 2 mm on average. Internode Length: Approximately 6 mm on average. Color: On young still elongating stems close to Yellow-Green Group 145B with overtones of Greyed-Yellow Group 160A. On maturing stems formed earlier in the season primarily near and through Greyed-Orange Group 177B with areas near and through Greyed-Orange Group 165A and 177A with highlights near and through Greyed-Orange Group 164A and 165A.

Foliage:

*Arrangement.*—Alternate.

*Configuration.*—Ranges from narrowly elliptic to narrowly ovate to ovate.

*Apex.*—Narrowly acute.

*Base.*—Broadly to narrowly cuneate.

*Length.*—Variable and from 5 mm to 3.5 cm.

*Width.*—Variable and from 3 mm to 1.5 cm.

*General aspect.*—Dense, small and bright yellow when young foliage is present.

*Color.*—The intensity of the leaf coloration varies with exposure to sunlight with more yellow and less green being apparent when the plant is grown in full sunlight. Young Foliage: On the upper surface depending upon light exposure near Yellow-Green Group 145A and 145B, and on the lower surface near Yellow-Green Group 144B. The upper surface of the foliage commonly includes substantial bright yellow coloration that is particularly pronounced when the plant is exposed to full sun. Mature Foliage: On the upper surface depending upon light exposure near Yellow-Green Group 144A, and on the lower surface depending upon light exposure near Yellow-Green Group 144B. The upper surface of the foliage commonly includes substantial bright yellow coloration that is particularly pronounced when the plant is exposed to full sun.

*Margin.*—Serrate.

*Petiole.*—Approximately 2 mm in length on average, approximately 0.8 mm in diameter on average on vigorously growing primary shoots, and approximately 0.4 to 0.6 mm (average approximately 0.5 mm) in diameter on smaller secondary stems, and the color commonly is near and shades through Yellow-Green Group 145A and 145B, and Yellow-Green Group 144C.

Inflorescence:

*Arrangement.*—Compound corymbs on stems of the current year's growth. The inflorescence commonly contains approximately 12 to 20 flowers.

*Bud shape.*—Globose to sub-globose.

*Bud size.*—Approximately 1.8 to 1.9 mm in length, and approximately 1.7 to 1.9 mm (average approximately 1.8 mm) in diameter.

*Bud texture.*—Commonly lightly covered with silvery-white villous to pilose hairs that are somewhat appressed and average approximately 0.3 mm in length.

*Bud color.*—Green Group 143D with Greyed-Red Group 182A and 182B at the tips.

*Flower color.*—Near Red Group 51C and Red Group 51D.

*Flower diameter.*—Approximately 5 mm with no appreciable depth when fully open in a flattened configuration.

*Type.*—Perfect (bisexual), polypetalous (i.e., the petals are completely separate).

*Petal shape.*—Suborbicular to broadly elliptical.

*Petal apex.*—Broadly obtuse to rounded.

*Petal base.*—Truncate.

*Petal margin.*—Entire and slightly undulate.

*Petal length.*—Approximately 1.8 mm on average when the flower is fully open.

*Petal width.*—Approximately 2 mm on average when the flower is fully open.

*Petal color.*—On both surfaces near Red-Purple Group 62C.

*Petal number.*—Five.

*Pistils.*—Five in number and approximately 1.5 mm in length.

*Stigma.*—Approximately 0.2 mm in size.

*Stamen.*—Approximately 25 or more in number.

*Filaments.*—Approximately 0.3 to 0.35 mm in length on average.

*Habit.*—Commonly blooms substantially continuously from May to October.

*Peduncle.*—Approximately 3 mm in length on average, approximately 0.5 mm in diameter on average, and the coloration is near and shading through Yellow-Green Group 147A, 147B, and 148B with a reddish tinge near Greyed-Purple Group 187B.

*Sepals.*—Five in number, obturbinatus, possess an acute apex, the margin is entire, approximately 1.1 mm in length from the apex to the point where the sepals unite, approximately 1.3 mm in width at the widest point where the sepals unite at the base, and on both surfaces the coloration is near and through Green Group 138A towards the apex and near and through Green Group 138D and shading near and through Greyed-Green Group 193A towards the base.

*Fruit/seed.*—During observations to date no fruit and seed production has been noted.

Development:

*Propagation.*—Propagates well through the rooting of cuttings.

*Disease resistance.*—Typical of *Spiraea.*

*Winter hardiness.*—Good, has over-wintered well in containers at West Grove, Pa., U.S.A., and in the ground at Earleville, Md., U.S.A. Performs well in U.S.D.A. Hardiness Zone No. 6.

Plants of the 'Conalex' cultivar have not been observed under all possible environmental conditions to date. Thus, the phenotypic expression may be found to vary somewhat with different light intensity and duration, cultural, and environmental conditions.

I claim:

1. A new and distinct *Spiraea japonica* plant having the following combination of characteristics:

(a) exhibits a dwarf mounding growth habit, (b) on a substantially continuous basis forms attractive medium-pink blossoms, (c) forms attractive light-green foliage that commonly includes substantial bright yellow coloration unlike the 'Lemondrop' variety (U.S. Plant Pat. No. 15,016), and well resists burning when present in full sun, and (d) displays good winter hardiness;

substantially as illustrated and described.

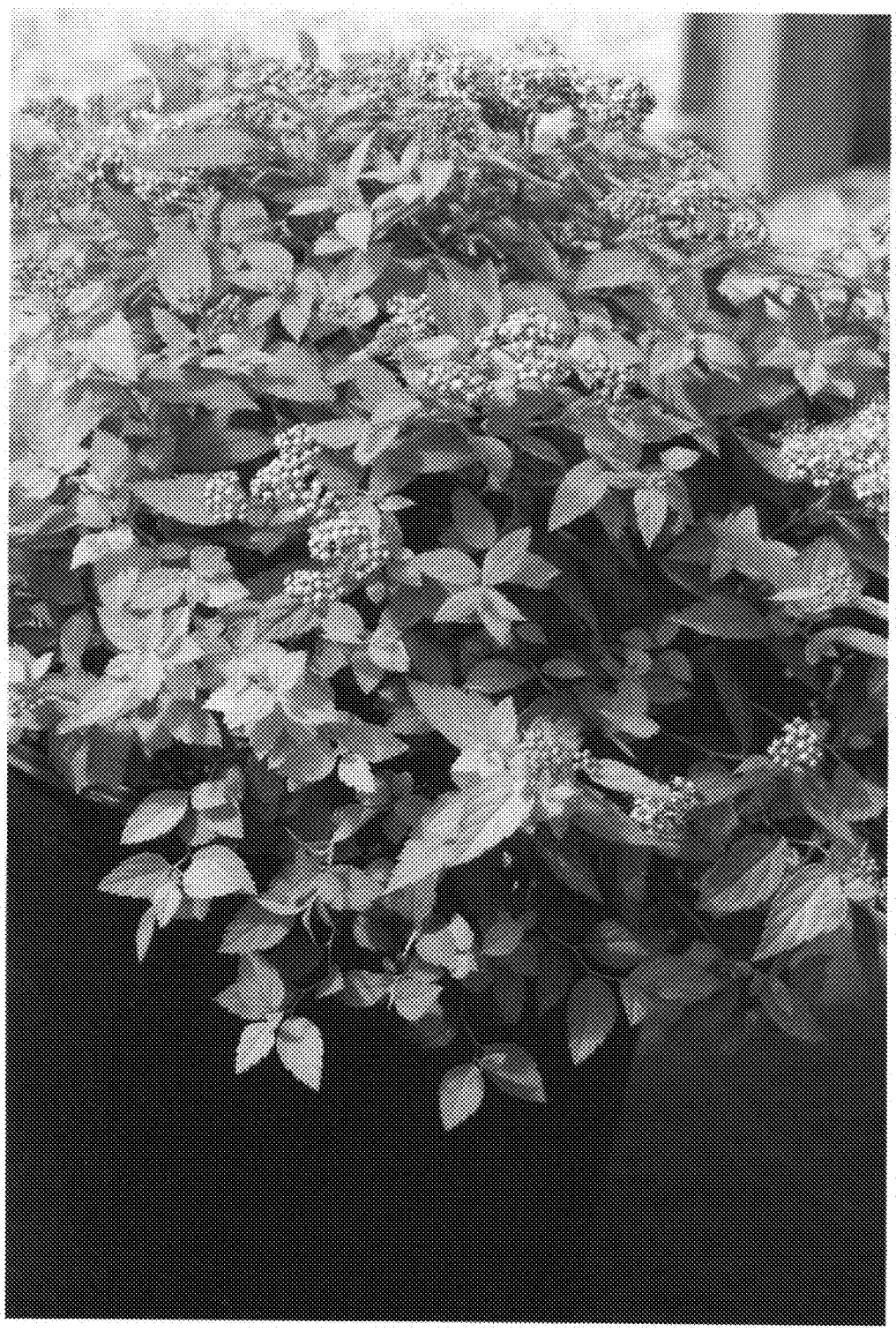

* * * * *